US009029816B2

United States Patent
Russell

(10) Patent No.: US 9,029,816 B2
(45) Date of Patent: May 12, 2015

(54) SYSTEM AND METHOD FOR EMITTING INFRARED RADIATION USING REFLECTED RADIATION TO ENHANCE EMISSION EFFICIENCY

(71) Applicant: Koninklijke Philips N.V., Eindhoven (NL)

(72) Inventor: James Torrance Russell, Bellevue, WA (US)

(73) Assignee: Koninklijkle Philips N.V., Eindhoven (NL)

( * ) Notice: Subject to any disclaimer, the term of this patent is extended or adjusted under 35 U.S.C. 154(b) by 0 days.

(21) Appl. No.: 14/362,948

(22) PCT Filed: Dec. 14, 2012

(86) PCT No.: PCT/IB2012/057343
§ 371 (c)(1),
(2) Date: Jun. 5, 2014

(87) PCT Pub. No.: WO2013/093746
PCT Pub. Date: Jun. 27, 2013

(65) Prior Publication Data
US 2014/0306129 A1    Oct. 16, 2014

Related U.S. Application Data

(60) Provisional application No. 61/577,123, filed on Dec. 19, 2011.

(51) Int. Cl.
*G21G 4/00* (2006.01)
*A61N 5/06* (2006.01)
*G01J 3/10* (2006.01)
*H05G 2/00* (2006.01)
*G01N 21/3504* (2014.01)
*G01J 3/02* (2006.01)
*A61M 16/10* (2006.01)

(52) U.S. Cl.
CPC .............. *G01J 3/108* (2013.01); *G01N 21/3504* (2013.01); *G01J 3/0216* (2013.01); *A61M 2016/102* (2013.01)

(58) Field of Classification Search
USPC ............... 250/338.1, 339.06, 339.11, 339.14, 250/341.8, 493.1, 495.1, 503.1, 504 R
See application file for complete search history.

(56) References Cited

U.S. PATENT DOCUMENTS

| 4,724,329 A | 2/1988 | Doyle et al. | |
| 4,803,370 A | 2/1989 | Eckles | |
| 2009/0302766 A1* | 12/2009 | Behr et al. | 315/82 |
| 2012/0242980 A1* | 9/2012 | Russell | 356/51 |

OTHER PUBLICATIONS

D.C. Laine et al, "Pulsed wideband IR thermal source", IEE Proceedings—Optoelectronics, vol. 144, No. 5, Oct. 1997, p. 315.

* cited by examiner

*Primary Examiner* — Bernard E Souw

(57) ABSTRACT

A source assembly (48) configured to generate infrared electromagnetic radiation includes an emitter (60) that emits electromagnetic radiation over an emission solid angle. A portion of the emitted electromagnetic radiation is used in a detection. The portion of the user electromagnetic radiation surrounds the optical path in a usable solid angle. Electromagnetic radiation outside of the usable solid angle is focused back by a reflection assembly (64) onto the emitter to enhance the efficiency of the emitter.

13 Claims, 5 Drawing Sheets

SYSTEM AND METHOD FOR EMITTING INFRARED RADIATION USING REFLECTED RADIATION TO ENHANCE EMISSION EFFICIENCY

CROSS-REFERENCE TO PRIOR APPLICATIONS

This application is the U.S. National Phase application under 35 U.S.C. §371 of International Application No. PCT/IB2012/057343, filed on Dec. 14, 2012, which claims the benefit of U.S. Provisional Patent Application No. 61/577,123, filed on Dec. 19, 2011. These applications are hereby incorporated by reference herein.

BACKGROUND

1. Field

The present disclosure pertains to a method and apparatus for generating infrared electromagnetic radiation for use in a system configured to detect relative amounts of one or more molecular species in a fluid.

2. Description of the Related Art

There are existing systems configured to monitor composition of flows of breathable gas being delivered to subjects. Some such systems rely on optical detection of composition. Typically, a beam of electromagnetic radiation is transmitted through a sample of the flow of breathable gas in question, and an optical detector on the other side measures a one or more parameters of the electromagnetic radiation after it has passed through the flow of breathable gas. The one or more parameters may include, for example, an optical band edge, band transmission, or band absorption. Such arrangements are known as non-dispersive (ND) systems.

The sources of electromagnetic radiation in these systems usually generate electromagnetic radiation across a larger solid angle than is actually used in the measurement. Electromagnetic radiation that is emitted outside of the solid angle being used is generally lost, or not used for a practical purpose by conventional systems.

SUMMARY

Accordingly, one or more aspects of the present disclosure relate to an infrared source assembly. In some embodiments, the source assembly comprises an emitter and a reflection assembly. The emitter is configured to emit infrared electromagnetic radiation along an optical path, wherein the emitter emits infrared electromagnetic radiation over an emission solid angle. A portion of the emitted infrared electromagnetic radiation that is usable along the optical path is emitted over a usable solid angle that is smaller than the emission solid angle such that the emission solid angle subsumes the usable solid angle. The reflection assembly is configured to reflect at least a portion of the emitted infrared electromagnetic radiation that is outside of the usable solid angle such that the reflected infrared electromagnetic radiation is focused at or near the emitter, thereby increasing the heat of the emitter.

Yet another aspect of the present disclosure relates to a method of emitting infrared electromagnetic radiation. In some embodiments, the method comprises emitting infrared electromagnetic radiation from an emissive surface along an optical path, wherein the infrared electromagnetic radiation is emitted over an emission solid angle, and wherein a portion of the emitted infrared electromagnetic radiation that is usable along the optical path is emitted over a usable solid angle that is smaller than the emission solid angle such that the emission solid angle subsumes the usable solid angle; and reflecting at least a portion of the emitted infrared electromagnetic radiation that is outside of the usable solid angle such that the reflected infrared electromagnetic radiation is focused at or near the emissive surface, thereby increasing heat at or near the emissive surface.

Still another aspect of present disclosure relates to a system configured to emit infrared electromagnetic radiation. In some embodiments, the system comprises means for emitting infrared electromagnetic radiation along an optical path, wherein the infrared electromagnetic radiation is emitted over an emission solid angle, and wherein a portion of the emitted infrared electromagnetic radiation that is usable along the optical path is emitted over a usable solid angle that is smaller than the emission solid angle such that the emission solid angle subsumes the usable solid angle; and means for reflecting at least a portion of the emitted infrared electromagnetic radiation that is outside of the usable solid angle such that the reflected infrared electromagnetic radiation is focused at or near the means for emitting, thereby increasing heat of the means for emitting.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
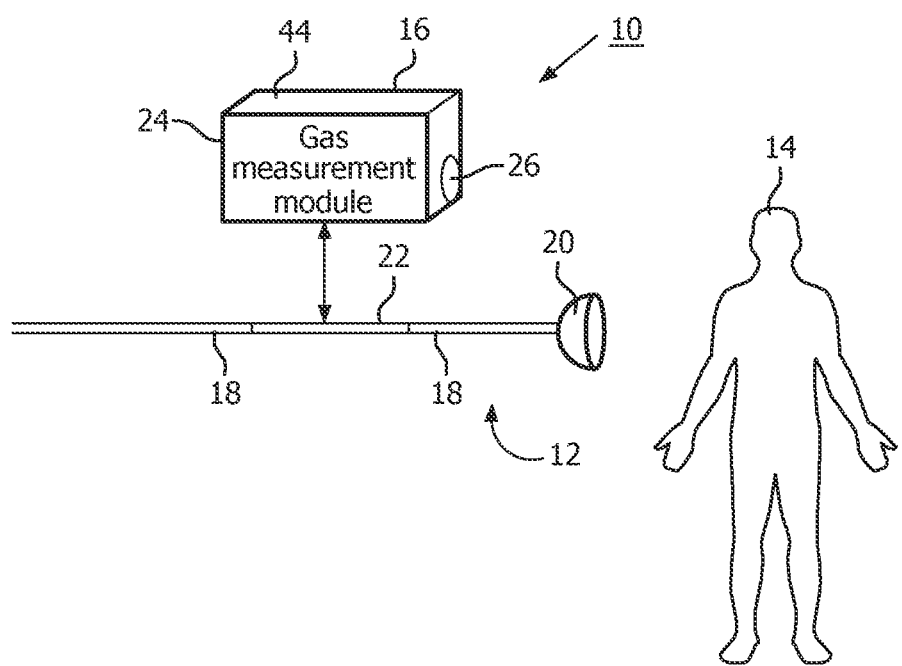
FIG. 1 is a system configured to monitor composition of a flow of breathable gas being delivered to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to analyze the composition of gas within a respiratory circuit 12 from which a subject 14 may receive ventilation therapy. In one embodiment, the respiratory circuit 12 is connected at one end to a pressure generator configured to generate a pressurized flow of breathable gas for delivery to the airway of subject 14 through respiratory circuit 12. However, this is not intended to be limiting. In one embodiment, system 10 includes a gas measurement module 16.

The respiratory circuit 12 includes a circuit conduit 18 and a subject interface appliance 20. In a number of different therapeutic scenarios, an airway of subject 14 is engaged to place respiratory circuit 12 in fluid communication with the airway of subject 14. The airway of subject 14 is engaged, and placed in fluid communication with respiratory circuit 12, by subject interface appliance 20. The subject interface appliance 20 may engage one or more orifices of the airway of subject 14 in a sealed or unsealed manner. Some examples of subject interface appliance 20 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The circuit conduit 18 is configured to convey gas toward and away from subject interface appliance 20. By way of non-limiting example, circuit conduit 18 may include a flexible conduit. For the purposes of this disclosure, circuit conduit 18 is not necessarily limited to a tubular member that conveys pressurized gas flows to and/or from subject interface appliance 20. The circuit conduit 18 may include any hollow body, container, and/or chamber placed in fluid communication with the airway of subject 14 by subject interface appliance 20.

Figure 2:
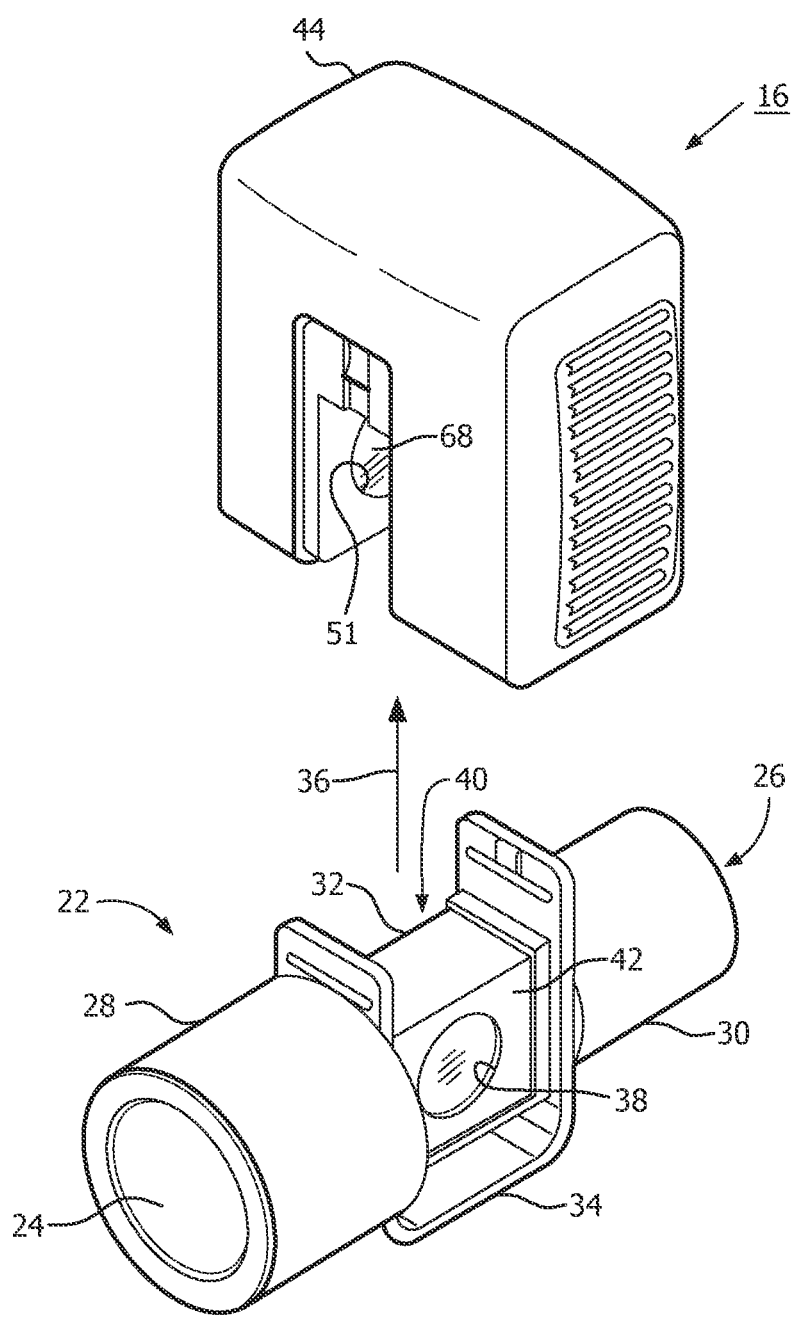
FIG. 2 is an airway adapter and gas measurement module.

The circuit conduit 18 includes a dock to which gas measurement module 16 can be removably coupled. The dock is formed in some embodiments by an airway adapter 22 included in circuit conduit 18. By way of illustration, FIG. 2 is an exploded view of airway adapter 22 and gas measurement module 16. Airway adaptor 22 includes a first opening 24 and a second opening 26, and is configured to form a flow path therebetween such that the flow of breathable gas within respiratory circuit 12 is conveyed through airway adapter 22. Airway adapter 22 can be a one-piece unit molded from Valox polyester and/or other polymers. Airway adapter 22 has a generally parallelepipedal center section 32 and two cylindrical end sections 28 and 30 that form first opening 24 and second opening 26, respectively. End sections 28 and 30 are axially aligned with center section 32.

The central section 32 of airway adapter 22 provides a seat for gas measurement module 16. An integral, U-shaped casing element 34 positively locates gas measurement module 16 endwise of airway adapter 22 and, also, in that transverse direction indicated by arrow 36 in FIG. 1. Arrow 36 also shows the direction in which airway adapter 22 is displaced to assemble it to gas measurement module 16. Windows 38 are formed in the center section 32 of airway adapter 22 on a first side 40 and a second side 42 of airway adapter 22. Windows 38 are formed from one or more materials that are optically transmissive for infrared electromagnetic radiation. With gas measurement module 16 assembled to airway adapter 22, these windows 38 are aligned along an optical path that is discussed further herein. That optical path extends from first side 40 to second side 42 transversely across the flow path formed by airway adapter 22 and the gas(es) flowing therethrough.

The gas measurement module 16 is configured to analyze the composition of gas within respiratory circuit 12. The gas measurement module 16 includes a housing 44 that houses and/or carries optical and/or electronic components that facilitate analysis of the composition of the gas within the sampling chamber formed by gas measurement module 16. Specifically, gas measurement module 16 is configured to direct infrared electromagnetic radiation across the sampling chamber of airway adapter 22 through windows 38, to receive the infrared electromagnetic radiation, and to generate output signals conveying information related to one or more parameters of the received electromagnetic radiation. The one or more parameters may include one or more of intensity, phase, flux, wavelength, and/or other parameters. These output signals can be used to determine composition of the gas within the sampling chamber.

Figure 3:
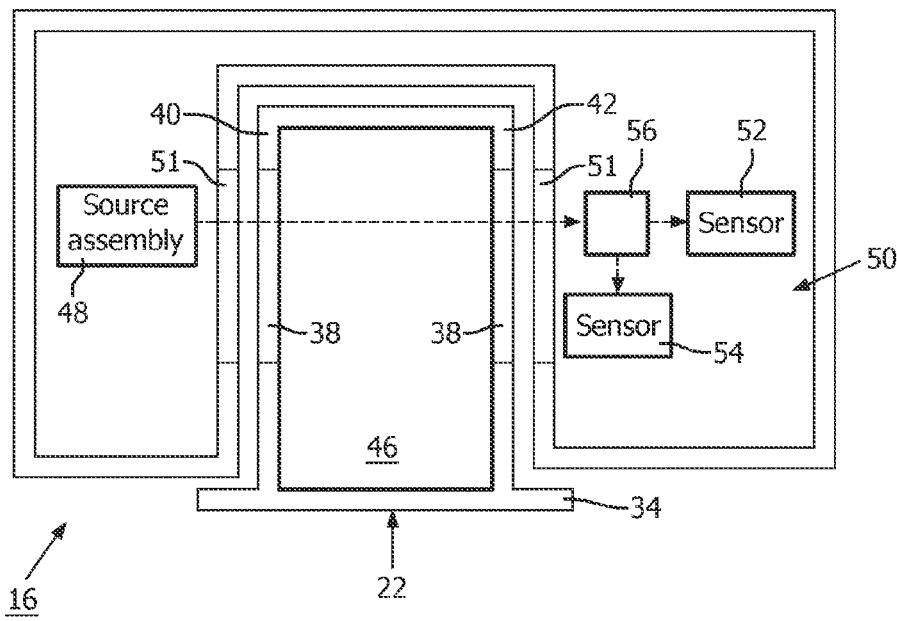
FIG. 3 is a is an airway adapter and gas measurement module.

By way of further illustration, FIG. 3 shows a schematic, sectional view of gas measurement module 16 and airway adapter 22 connected for operation. This view shows the sampling chamber 46 formed within airway adapter 22. As can be seen in each of FIGS. 2 and 3, housing 44 has a "U" shaped cross-section, and encloses a source assembly 48, a detector 50, and/or other components. Two opposing legs of the "U" shaped housing 44 define opposite sides of a gap therebetween. In the leg on one side of the gap source assembly 48 is disposed, and in the leg on the other side of the gap detector 50 is disposed. The gas measurement module 16 also includes self-contained electronics disposed within the housing 44 (not shown).

Formed in housing 44 are a pair of windows 51 that align with windows 38 when gas measurement module 16 is docked with airway adapter 22 in the manner shown in FIG. 3. Windows 51 are formed from one or more materials that are transmissive for infrared electromagnetic radiation such that infrared electromagnetic radiation can pass along an optical path through both windows 38 and 51 to travel between sampling chamber 46 and the interior of housing 44.

Source assembly 48 is a radiation source that produces broadband radiation including an "MWIR" (Mid-Wavelength InfraRed) band. Infrared radiation generally refers to radiation occupying a band of wavelengths in the optical spectrum between 0.7 µm and 300 µm. "MWIR" generally refers to a mid-wavelength subset of the infrared radiation band between 3 µm and 8 µm. MWIR radiation emitted by source assembly 48 includes a reference wavelength and a carbon dioxide wavelength ($\lambda_{REF}$ and $\lambda_{CO2}$, respectively). Source assembly 48 may operate substantially as a blackbody for at least a portion of the spectrum (e.g., between 0.7 µm and 300 µm).

Detector 50 includes two separate photosensitive sensors 52 and 54. The basic principle of operation behind Capnometry/Capnography via detector 50 is that infrared radiation in a band around 4.275 µm experiences increasing absorption (when traveling a fixed-length path through a sample gas) with increasing carbon dioxide concentration—according to a reliably repeatable relationship. By way of comparison, the absorption of 3.681 μm infrared radiation under the same conditions is essentially unaffected by carbon dioxide concentration.

When the MWIR radiation from source assembly 48 passes through the flow of breathable gas in sampling chamber 46, infrared radiation at $\lambda_{CO2}$ is attenuated according to the concentration of carbon dioxide in the flow of breathable gas. Infrared radiation at $\lambda_{REF}$, however, is unaffected by any carbon dioxide in the body of gas, and varies only with the intensity of the infrared radiation from source assembly 48. Infrared radiation at $\lambda_{REF}$ is directed to sensor 52 by a beam splitter 56, while infrared radiation at $\lambda_{CO2}$ is directed to sensor 54 by beam splitter 56. Since $\lambda_{REF}$ and $\lambda_{CO2}$ are fairly close together on the black-body radiation curve, the output signals of sensors 52 and 54, which are sensitive to IR electromagnetic radiation, will be approximately proportional to one another over small variations in source radiation intensity as long as carbon dioxide concentration in the body of gas remains constant. By "zeroing" detector 50 with $N_2$ (or with room air—after making appropriate compensation for residual carbon dioxide in the atmosphere), a reference ratio between the output signal levels from sensor 52 and sensor 54 is established. Whenever the ratio between the two signals is equal to this reference ratio, there is no carbon dioxide in sampling chamber 46. Any decrease in the output signal of sensor 54 relative to output signal of sensor 52 indicates a corresponding increase in the concentration of carbon dioxide in sampling chamber 46.

Figure 4:
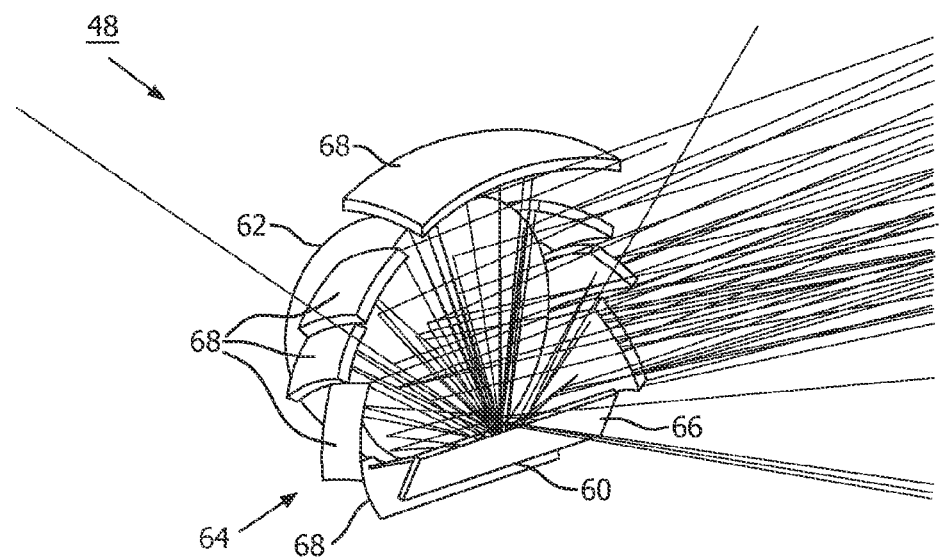
FIG. 4 illustrates a source assembly of a gas measurement module.
Figure 5:
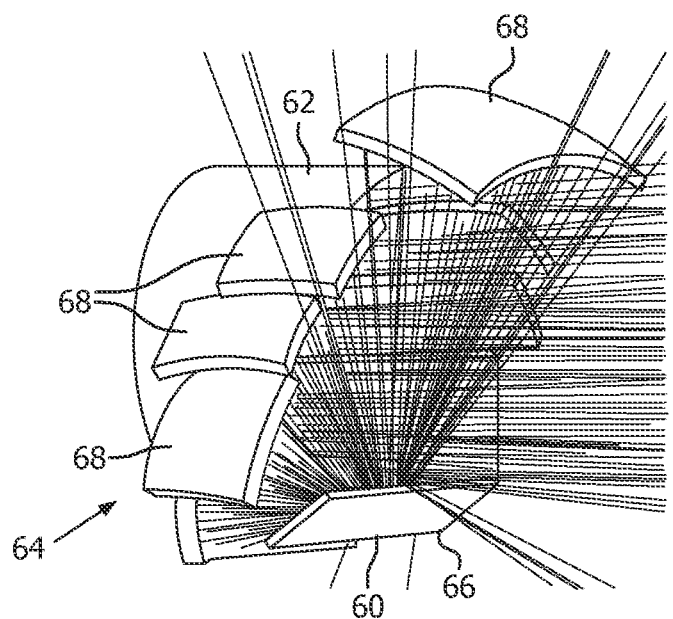
FIG. 5 illustrates a source assembly of a gas measurement module.
Figure 6:
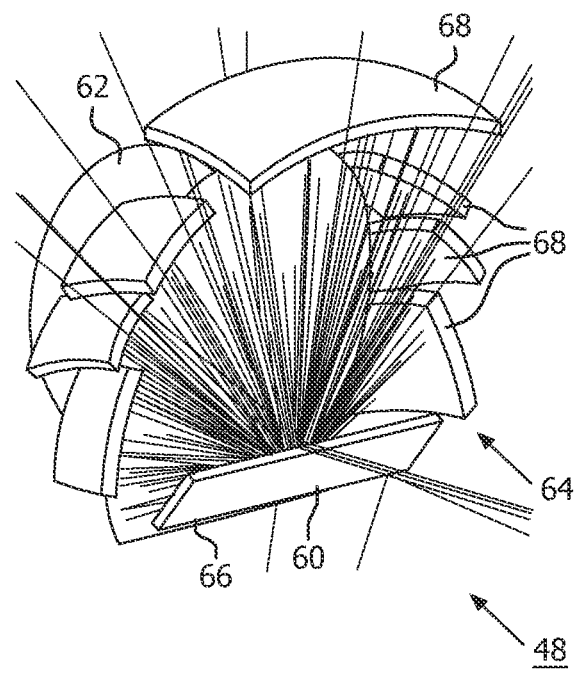
FIG. 6 illustrates source assembly of a gas measurement module.

In FIGS. 4-6, one or more embodiments of source assembly 48 are illustrated. As can be seen in FIGS. 4-6, source assembly 48 may include one or more of an emitter 60, collimating optics 62, a reflection assembly 64, and/or other components.

Emitter 60 is configured to emit infrared electromagnetic radiation along an optical path responsive to an electrical current being applied thereto. For example, emitter 60 may include a substrate 66 having an emissive element (not shown) printed thereon. Responsive to an electrical current being applied to the emissive element, the emissive element may heat up and emit infrared electromagnetic radiation. Emitter 60 emits the infrared electromagnetic radiation over an emission solid angle. The emission solid angle may be, for example, about 180°. The distribution of the emitted electromagnetic radiation over the emission solid angle may be Lambertian.

Collimating optics 62 are configured to receive a portion of the electromagnetic radiation emitted by emitter 60 along the optical path, and to collimate the received portion of the electromagnetic radiation along the optical path. In the embodiments illustrated in FIGS. 4-6, collimating optics 62 include a collimating mirror 70. This is not intended to be limiting, as other optics (e.g., one or more collimating lenses) may be implemented as collimating optics. The portion of electromagnetic radiation received by collimating optics 62 is electromagnetic radiation emitted within a usable solid angle of emitter 60. The usable solid angle of the emitter is smaller than the emission solid angle such that the emission solid angle subsumes the usable solid angle. The usable solid angle may be defined by the size, shape, and/or position of the collimating optics 62. Electromagnetic radiation within the emission solid angle that fall outside of the usable solid angle is generally made up of the electromagnetic radiation that is not received by the collimating optics. In conventional setups, the electromagnetic radiation within the portion of the emission solid angle that falls outside of the usable solid angle may be "lost" (e.g., not implemented to enhance the operation of system 10).

Reflection assembly 64 is configured to reflect at least a portion of the electromagnetic radiation that is outside of the usable solid angle back toward emitter 60. Reflection assembly 64 may be configured to focus the reflected electromagnetic radiation at or near emitter 60. This may include focusing the reflected electromagnetic radiation at the emissive surface formed by the emissive element on substrate 66.

In the one or more embodiments illustrated in FIGS. 4-6, reflection assembly 64 may include a plurality of reflectors 68. Reflectors 68 are arranged around the optical path to receive at least a portion of the electromagnetic radiation that is outside of the usable solid angle. Reflectors 68 may be configured such that electromagnetic radiation that becomes incident on reflectors 68 at a first location is focused on a different portion of emitter 60 (e.g., a different location on the emissive surface of the emissive element, a different location on the substrate, and/or other different portions) than electromagnetic radiation that becomes incident on reflectors 68 at a second location. This may enhance and/or maintain a uniformity of the heat applied to emitter 60 by the electromagnetic radiation focused by reflection assembly 64. It will be appreciated that this configuration for reflection assembly 64 is not intended to be limiting. In some embodiments, rather than the reflectors 68 shown in FIGS. 4-6, reflection assembly 64 includes one or more mirrors (e.g., a single mirror) manufactured to provide a contiguous reflective surface around at least a portion of the usable solid angle.

Reflection assembly 64 may be configured to receive electromagnetic radiation over a reflected solid angle. In some embodiments, the reflected solid angle begins at the end of the usable solid angle, and continues to the greatest angle from the optical path at which electromagnetic radiation is received by reflection assembly 64. This greatest angle may be less than the emission solid angle, as electromagnetic radiation at relatively high angles will tend to have low intensity in some distributions, such as a Lambertian distribution. This greatest angle may be less than about 90°, less than about 80°, less than able 70°, less than about 60°, and/or have other values. The percentage of electromagnetic radiation outside of the usable solid angle that is received by reflection assembly 64, and focused back onto emitter 60 may be at least 30%, at least 40%, at least 50%, at least 60%, at least 70%, at least 80%, and/or other percentages.

Reflecting electromagnetic radiation outside of the usable solid angle may enhance the efficiency of emitter 60. Further, in embodiments in which emitter 60 is being driven with pulses of current, the reflected electromagnetic radiation will tend to increase heat in substantial synchronicity with the current pulses. This will facilitate the modulation of heat of emitter 60 by the pulses of current.

Figure 7:
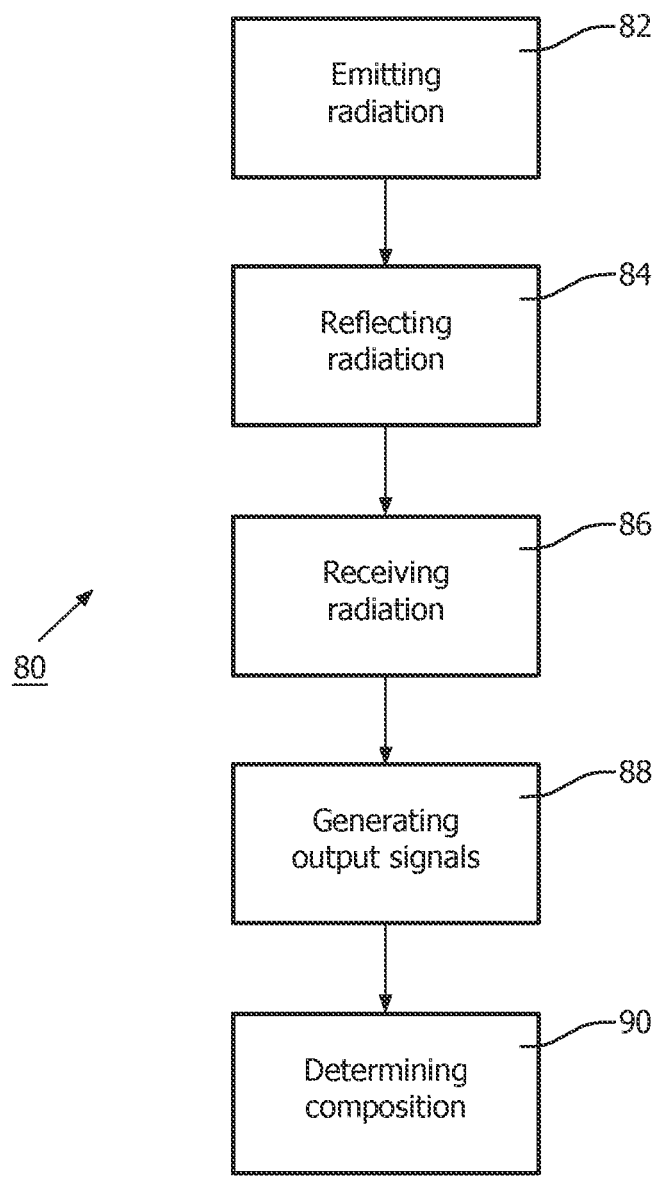
FIG. 7 illustrates a method of generating infrared electromagnetic radiation.

FIG. 7 illustrates a method 80 of monitoring composition of a flow of breathable gas within a respiratory circuit that is in fluid communication with an airway of a subject. The operations of method 80 presented below are intended to be illustrative. In some embodiments, method 80 may be accomplished with one or more additional operations not described, and/or without one or more of the operations discussed. Additionally, the order in which the operations of method 80 are illustrated in FIG. 7 and described below is not intended to be limiting.

At an operation 82, infrared electromagnetic radiation is generated. The infrared electromagnetic radiation is emitted from an emissive surface along an optical path. The electromagnetic radiation is emitted over an emission solid angle.

The portion of the emitted electromagnetic radiation that is used along the optical path is emitted over a usable solid angle that is smaller than the emission solid angle such that the emission solid angle subsumes the usable solid angle. In some embodiments, operation 82 is performed by an emitter the same as or similar to emitter 60 (shown in FIGS. 4-6 and described herein).

At an operation 84, at least a portion of the emitted electromagnetic radiation that is outside of the usable solid angle is reflected. This reflection focuses the electromagnetic radiation at or near the emissive surface, thereby increasing heat at or near the emissive surface. In some embodiments, operation 84 is performed by a reflection assembly the same as or similar to reflection assembly 64 (shown in FIGS. 4-6 and described herein).

At an operation 86, electromagnetic radiation emitted through the usable solid angle that has passed through a flow of breathable gas is received. In some embodiments, operation 86 is performed by a detector assembly the same as or similar to detector assembly 50 (shown in FIG. 3 and described herein).

At an operation 88, output signals conveying information to one or more parameters of the received electromagnetic radiation are generated. in some embodiments, operation 88 is performed by a detector assembly the same as or similar to detector assembly 50 (shown in FIG. 3 and described herein).

At an operation 90, information related to the composition of the flow of breathable gas is determined from the output signals. This information may include a relative amount, concentration, and/or level of one or more molecular species within the flow of breathable gas. In some embodiments, operation 90 is performed by one or more processors that receive the output signals.

It will be appreciated that the description herein of source assembly 48 being disposed in a system configured to detect carbon dioxide in a respiratory circuit is not intended to be limiting. The principles described herein may be implemented to enhance the performance of sensors of various molecular species in various types of fluids (e.g., gases, liquids, and/or other fluids) in various contexts. The description of a system configured to detect carbon dioxide in a respiratory circuit is merely an exemplary implementation.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An infrared source assembly, the source assembly comprising:
    an emitter configured to emit infrared electromagnetic radiation along an optical path, wherein the emitter defines an emission solid angle over which the infrared electromagnetic radiation is emitted, and wherein a portion of the emitted infrared electromagnetic radiation that is usable along the optical path defines a usable solid angle that is smaller than the emission solid angle such that the emission solid angle subsumes the usable solid angle; and
    a reflection assembly configured to reflect at least a portion of the emitted infrared electromagnetic radiation that is outside of the usable solid angle such that the reflected infrared electromagnetic radiation is focused at or near the emitter, thereby increasing heat of the emitter.

2. The source assembly of claim 1, wherein the reflection assembly comprises at least one focusing mirror.

3. The source assembly of claim 1, wherein the reflection assembly configured to focus at least 30% of the emitted infrared electromagnetic radiation that is outside of the usable solid angle.

4. The source assembly of claim 1, wherein the reflection assembly is configured such that infrared electromagnetic radiation reflected from different locations is focused at different locations on the emitter.

5. The source assembly of claim 1, wherein the reflection assembly forms a single substantially continuous reflective surface that reflects the emitted infrared electromagnetic radiation.

6. A method of emitting infrared electromagnetic radiation, the method comprising;
    emitting infrared electromagnetic radiation from an emissive surface along an optical path, wherein the infrared electromagnetic radiation is emitted over an emission solid angle defined by the emissive surface, and wherein a portion of the emitted infrared electromagnetic radiation that is usable along the optical path defines a usable solid angle that is smaller than the emission solid angle such that the emission solid angle subsumes the usable solid angle; and
    reflecting at least a portion of the emitted infrared electromagnetic radiation emitted over the emission solid angle that is outside of the usable solid angle to focus the reflected infrared electromagnetic radiation at or near the emissive surface, thereby increasing heat at or near the emissive surface.

7. The method of claim 6, wherein the reflecting operation is performed by at least one focusing mirror.

8. The method of claim 6, wherein, reflecting, at least a portion of the emitted infrared electromagnetic radiation comprises reflecting at least 30% of the emitted infrared electromagnetic radiation that is outside of the usable solid angle to be focused at or near the emissive surface.

9. The method of claim 6, wherein infrared electromagnetic radiation that is reflected from different locations is focused at different locations on the emitter.

10. The method of claim 6, wherein the reflecting operation is performed by a single substantially continuous reflective surface that reflects the emitted infrared electromagnetic radiation.

11. The source assembly of claim 1, further comprising:
    collimating optics configured to collimate the portion of the emitted infrared electromagnetic radiation emitted over the usable solid angle.

12. The source assembly of claim 1, wherein the collimating optics defines the portion of the emitted infrared electromagnetic radiation that is usable along the optical path.

13. The source assembly of claim 1, wherein the reflection assembly comprises a plurality of reflectors arranged around the optical path to receive the at least a portion of the electromagnetic radiation that is outside of the usable solid angle.

\* \* \* \* \*